United States Patent [19]

Baiocchi

[11] 4,097,522

[45] Jun. 27, 1978

[54] SYNTHESIS OF M-BENZOYL-HYDRATROPIC ACID

[75] Inventor: Leandro Baiocchi, Rome, Italy

[73] Assignee: Aziende Chimiche Riunite Angelini Francesco A.C.R.A.F. S.p.A., Rome, Italy

[21] Appl. No.: 690,832

[22] Filed: May 28, 1976

[30] Foreign Application Priority Data

Jun. 5, 1975 Italy ............................. 49925 A/75

[51] Int. Cl.$^2$ ............................................. C07C 65/20
[52] U.S. Cl. ............................. 260/517; 260/343.3 R; 260/515 R
[58] Field of Search ................. 260/515, 517, 343.3 R

[56] References Cited

FOREIGN PATENT DOCUMENTS 622,405  2/1933  Germany .......................... 260/343.3

*Primary Examiner*—Jane S. Myers
*Attorney, Agent, or Firm*—Ladas, Parry, Von Gehr, Goldsmith & Deschamps

[57] ABSTRACT

A process is provided for the production of m-benzoyl-hydratropic acid which comprises heating the reaction mixture obtained from the condensation of 2-benzoyl-cyclohexanone and pyruvic acid, its esters or salts, at a temperature of 200° to 230° and in the presence of an acid catalyst.

5 Claims, No Drawings

SYNTHESIS OF M-BENZOYL-HYDRATROPIC ACID

BACKGROUND OF THE INVENTION

1. Field of the Invention

The present invention relates to a new synthesis of m-benzoyl-hydratropic acid (I), a substance which has found wide use in human therapy.

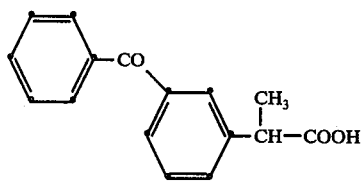

2. The Prior Art

Notwithstanding the fact that three syntheses of this compound are already known, these processes suffer notable disadvantages from an industrial point of view.

In particular, the first process according to French Pat. No. 1,546,478 requires a multiplicity of steps and the use of substances which are either highly toxic (KCN) or irritant (m-benzoyl-benzyl bromide) while the second process and the third process according to French Pat. No. 1,546,478, (I addition of Dec. 15, 1967) and according to French Pat. No. 2,163,875 appear clearly, by the description contained in the specifications, themselves limited mainly to laboratory use, with little possibility of industrial application.

OBJECTS OF THE INVENTION

It is an object of the invention to provide a novel synthetic process for obtaining m-benzoyl hydratropic acid (I) in a two-step process with higher yields than known processes have achieved from readily available materials.

It is a further object of the invention to provide a novel intermediate in the said novel synthetic process, namely, the new compound 7-benzoyl-3-methyl-2,4,5,6-tetrahydro-benz[b]-furan-2-one.

DESCRIPTION OF THE INVENTION

The synthesis of I which is described in the present application utilized a completely original reaction which permits the preparation of m-benzoyl-hydratropic acid in only two steps and with good yields, from readily available materials. The crucial point of the invention consists in the aromatization steps, at a temperature between 200° and 230° and in the presence of a suitable acid catalyst, of the condensation product or mixture of condensation products which are obtained from 2-benzoyl-cyclohexanone (II) and pyruvic acid (III, R = H) or by one of its simple derivatives (ester or alkaline metal salt) according to the following scheme:

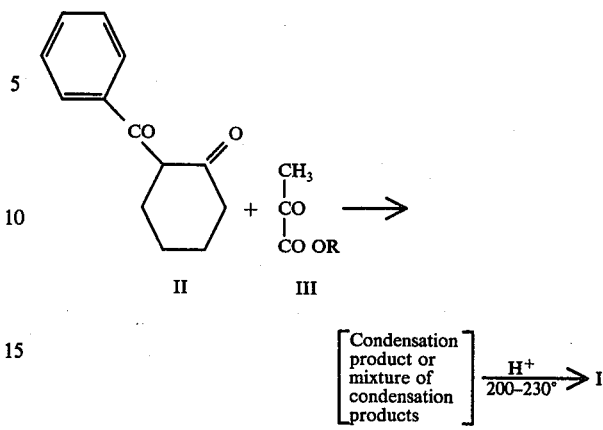

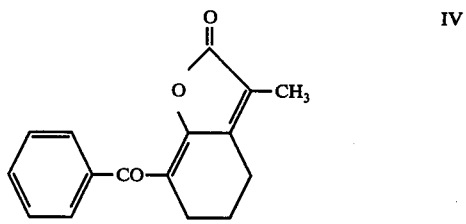

The condensation of 2-benzoyl-cyclohexanone with the pyruvic acid (or its derivatives) is carried out at about 150° and does not require the use of solvents.

It is possible to use as catalysts acid materials (HCl, $ZnCl_2$, $Al_2O_3$, etc.), basic materials (triethylamine, NaOH, etc.), surfactants (sodium dodecylsulfonate and the like), acetic anhydride, or mixtures thereof.

The nature of the products obtained depends both on the nature of the pyruvic acid derivative and on the catalyst used to promote the condensation.

In some of these conditions one condensation product predominates with respect to the others. It can be separated by chromatography on $SiO_2$ column, or by traditional techniques, depending on the complexity of the mixture obtained. The elemental analysis and the spectrophotometric properties of this product are in agreement with the lactonic structure (IV) of 7-benzoyl-3-methyl-2,4,5,6-tetrahydro-benzo[b]-furan-2-one.

This lactone subjected to aromatization under the conditions hereinafter described gives m-benzoyl-hydratropic acid in almost quantitative yields.

On the other hand, when some untreated condensation mixtures are subjected to aromatization, there is obtained m-benzoyl-hydratropic acid in yields better than could be justified considering the actual content of IV in the mixtures themselves. It is therefore evident that in these mixtures there are present, together with lactone IV, other products containing one or more water molecules and capable of forming I during the successive aromatization.

The aromatization itself is carried out by simply heating lactone IV, or the mixtures of products obtained in the preceding condensations, at a temperature between 200° and 230°, in the presence of a large excess of an acid catalyst. The reaction time is variable between 5 and 24 hours and is determined by the type of catalyst used, the nature of which can vary considerably. In addition to polyphosphoric acid and aluminium trichloride one can employ with good results concentrated hydrochloric acid in a closed tube. However, from a practical point of view it is preferable to use pyridine hydrochloride or a mixture of hydrochlorides of commercial pyridyl bases. Such reactants present the advantage of not requiring closed reaction vessels and to have fair solvent properties with respect to the reaction mass.

The choice between the use of purified lactone IV or of the mixture of condensation products is dictated by the particular practical reasons. In the first case, in fact, it is possible to obtain very pure m-benzoyl-hydratropic acid, but in lower yields. In the second case the yields are generally better but it is sometimes necessary to separate the m-benzoyl-hydratropic acid from a certain quantity of other acids of lower molecular weight which are present therewith. Such purification is, however, easily realizable through precipitation and recrystallization of the salt of m-benzoyl-hydratropic acid with a secondary amine (diethylamine, diisopropylamine, dicyclohexylamine) or by the usual purification techniques.

The following examples are illustrative of the invention but not limitative thereof.

EXAMPLE I m-Benzoyl-hydratropic acid from
2-benzoyl-cyclohexanone and pyruvic acid A mixture of 10 g of 2-benzoyl-cyclohexanone, 5.8 g of pyruvic acid and 0.2 g of sodium dodecylsulfate is heated at 150° for 15 hours. After cooling, the raw reaction product is extracted with ethyl ether and the ether solution is washed with an aqueous solution of sodium bicarbonate, then with water and then dried. The residue which is obtained after removing the solvent (9 g) is chromatographed on an $SiO_2$ column using as an eluent cyclohexane: ethyl ether 7:3. There are obtained 3.2 g of 7-benzoyl-3-methyl-2,4,5,6-tetrahydro-benzo[b]furan-2-one. After recrystallization from hexane-ethyl acetate m.p. is 79°–81°.

Analysis: for $C_{16}H_{14}O_3$ Found % C, 75.59; H, 5.53; Calc. C, 75.57; H, 5.55.

NMR (in $CHCl_3$, TMS, s.i.) multiple between 7.3 and 8δ(5H): aromatic protons; single at 1.9δ(3H): methyl.

IR ($CHCl_3$) $\nu_{CO} = 1775$ cm$^{-1}$ (aromatic ketone).

A mixture of 5 g of the preceding product and of 25 g of pyridine hydrochloride are heated at 230° for 5 hours. It is then cooled and the reaction mass is poured into water. The oil which separates is crystallized by scratching. It is filtered, dried and recrystallized from hexane-benzene. Yield is 4 g m.p. 93°–94° even when mixed with an authentic sample.

EXAMPLE 2

7-Benzoyl-3-methyl-2,4,5,6-tetrahydro-benzo[b]furan-2-one from 2-benzoyl-cyclohexanone and ethyl pyruvate A mixture of 202 g of 2-benzoyl-cyclohexanone, 348 g of ethyl pyruvate, 4.1 g of sodium dodecylsulfate and 51 ml of acetic anhydride is heated at 160°–170° for 40 hours, removing the volatile portion which is produced. After cooling, the reaction mass is taken up with ethyl ether, the ether solution is washed with a sodium bicarbonate solution, then with water and then evaporated to dryness. Anything distilling up to 155° under a pressure of 1mm/Hg is removed therefrom. The residue (183 g) is dissolved by heating in 150 ml of methanol and the solution is left in a refrigerator overnight. There are obtained 113 g of product m.p. 73°–77°.

This product treated with 5 parts of pyridine hydrochloride, as described in Example 1, gives 100 g of a raw product which after crystallization from hexane-ethyl acetate give 69 g of m-benzoyl-hydratropic acid m.p. 91°–95°. Another 15–20 g of product are obtained by recovery from the mother liquors.

EXAMPLE 3 m-Benzoyl-hydratropic acid from the mixture of the products of the condensation of
2-benzoyl-cyclohexanone and ethyl pyruvate A mixture of 20 g of 2-benzoyl-cyclohexanone, 21.6 g of ethyl pyruvate and 0.2 g of p-toluenesulfonic acid is heated at 150° for 15 hours. There is removed that fraction which distills at 1 mm (Hg up to 150°) and the residue is heated for 10 hours at 230° with 5 parts by weight of pyridine hydrochloride. After cooling the raw reaction products are poured in water and extracted with ether. The residue which is obtained after evaporation of the solvent is steam distilled. The part which does not distil is extracted with ether, the ether solution is dried well over sodium sulfate and to the dried solution there is added diethylamine until a clearly alkaline pH is reached. There thus precipitates a mixture of diethylamine salts from which, through fractional crystallization with hexane-ethyl acetate there is obtained the diathylamine salt of m-benzoyl-hydratropic acid m.p. 102°–104°. The free acid is obtained therefrom with the usual techniques.

What is claimed is:

1. A process for the production of m-benzoyl hydratropic acid which comprises (a) condensing 2-benzoyl cyclohexanone and a compound selected from the group consisting of pyruvic acid and its ester to obtain a reaction mixture containing as a reaction product 7-benzyol-3-methyl-2,4,5,6-tetrahydro-benzo[b]-furan-2-one, and then (b) heating the reaction mixture at a temperature of 200° to 230° C in the presence of a large excess of an acid catalyst.

2. A process according to claim 1 wherein said condensing is effected at a temperature of about 150° C.

3. A process according to claim 2 wherein said condensing is effected in the presence of an acid or a surfactant.

4. A process according to claim 1 wherein said 7-benzoyl-3-methyl-2,4,5,6-tetrahydro-benzo[b] furan-2-one is recovered from the condensation mixture and then heated as indicated to yield the desired product.

5. A process according to claim 1 wherein said acid catalyst is pyridine hydrochloride.

* * * * *